(12) United States Patent
Lee-Alvarez et al.

(10) Patent No.: US 6,375,900 B1
(45) Date of Patent: Apr. 23, 2002

(54) CARBON ANALYZER WITH IMPROVED CATALYST

(75) Inventors: Maria Theresa Lee-Alvarez, West Chester; Robert A. Booth, Cincinnati, both of OH (US)

(73) Assignee: Tekmar Company, Mason, OH (US)

( * ) Notice: Subject to any disclaimer, the term of this patent is extended or adjusted under 35 U.S.C. 154(b) by 0 days.

(21) Appl. No.: 09/300,234

(22) Filed: Apr. 27, 1999

(51) Int. Cl.[7] ............................................... G01N 31/12
(52) U.S. Cl. ........................ 422/80; 422/68.1; 422/78; 436/145; 436/146; 436/159
(58) Field of Search ........................ 422/68.1, 78, 80, 422/83, 94, 129, 130, 131; 436/145, 146, 159, 178

(56) References Cited

U.S. PATENT DOCUMENTS

| | | | |
|---|---|---|---|
| 4,355,056 A | 10/1982 | Dalla Betta et al. | 427/126.4 |
| 4,619,902 A | * 10/1986 | Bernard | 436/135 |
| 5,106,754 A | * 4/1992 | Steele et al. | 436/146 |
| 5,271,900 A | 12/1993 | Morita | 422/80 |
| 5,425,919 A | 6/1995 | Inoue et al. | 422/67 |
| 5,501,801 A | * 3/1996 | Zhang et al. | 210/748 |
| 5,620,610 A | 4/1997 | Ishii et al. | 210/763 |
| 5,820,823 A | 10/1998 | Godec et al. | 422/78 |

OTHER PUBLICATIONS

"Measuring Carbon in Salty Waters", Methods & Application Notes, Copyright 1999, Tekmar Dohrman, TOC–010, Rev. Oct. 1995, pp. 1–2.
"The History of Laboratory TOC Analyzers", Shimadzu Products, pp. 1–2., printed from www site http://www.s-si.shimadzu.com/products/4_total_organic_carbon/toch-is.html, on Apr. 16, 1999.
"Total Organic carbon", Method 9060, Sep. 1986, pp. 1–5.

\* cited by examiner

*Primary Examiner*—Jill Warden
*Assistant Examiner*—Dwayne K. Handy
(74) *Attorney, Agent, or Firm*—Westman, Champlin & Kelly, P.A.

(57) ABSTRACT

A carbon analyzer, is provided which includes a combustion chamber having a platinum on titania catalyst. The combustion chamber and catalyst are also provided. A method for analyzing carbon-containing specimens with such an analyzer is also provided as well as a method for oxidizing such specimens with a platinum on titania catalyst. A method of conditioning the catalyst is also provided.

9 Claims, 6 Drawing Sheets

CARBON ANALYZER WITH IMPROVED CATALYST

BACKGROUND OF THE INVENTION

Carbon analyzers are used in a variety of industries to provide analytical information relating to carbon concentration in a given specimen. Such industries include the chemical, pharmaceutical, food, and beverage industries. Carbon analyzers are also frequently used in the analysis of drinking water, groundwater, wastewater and soils in order to test for contaminants and to ensure compliance with governmental regulations.

There are generally two types of carbon present in a given specimen, organic carbon such as complex hydrocarbons or pesticides and inorganic carbon such as carbonate and bicarbonate. The organic carbon and inorganic carbon comprise the total carbon of a specimen. Thus, if total organic carbon is the quantity of interest it can be obtained by subtracting the inorganic carbon value from the total carbon value. EPA Method 9060, published September 1986, provides further reference relating to total organic carbon measurement.

Carbon analyzers themselves generally fall into one of two categories depending upon the manner in which they convert the specimen, through oxidation, into water and carbon dioxide. The first type is known as wet chemical oxidation analyzers. Wet chemical oxidation analyzers oxidize a specimen by subjecting it to a chemical environment such as persulfate while bombarding the specimen with ultraviolet radiation. An example of such an analyzer is the Phoenix 8000™ analyzer available from Tekmar-Dohrmann, of Cincinnati, Ohio. The second type is known as combustion analyzers. These analyzers subject the specimen to an elevated temperature, sometimes as high as about 1000 degrees Celsius to oxidize the specimen. An example of this type of analyzer is the model DC-190™ Combustion TOC Analyzer also available from Tekmar-Dohrmann. For either type of analyzer, the net result is theoretically complete oxidation of the specimen.

Different analyzers and methodologies lend themselves better to different applications. Combustion analyzers are generally able to more effectively oxidize high molecular weight specimens. One limitation of combustion analyzers, however, had been the effects of matrices such as salt water upon the combustion chamber itself. At such high temperatures, sodium chloride has a devitrifying effect on quartz glassware, as well as other undesirable effects. One solution for such matrices as well as most other matrices has been to provide a e catalyst in the combustion chamber which lowers the activation temperature of the specimen thus providing better oxidation at lower temperatures. For example, when the specimen is exposed to platinum (Pt) on alumina ($Al_2O_3$) as a catalyst, the temperature can be reduced to about 670 degrees Celsius. This lower temperature operation ameliorates some of the difficulties with matrices such as salt water.

As lab automation and technology in general have progressed, there is an increasing need to provide accurate and repeatable carbon analysis more rapidly thus reducing cycle time and increasing throughput.

SUMMARY OF THE INVENTION

A combustion carbon analyzer includes a combustion chamber having a platinum on titania ($TiO_2$) catalyst. A method of oxidizing a carbon-containing specimen is also provided which includes exposing the specimen to a catalyst comprising platinum on titania. A method of conditioning the catalyst to remove carbon is also provided.

Embodiments of the invention provide quicker analyses thus reducing cycle time and increasing throughput. Further, catalysts of embodiments of the invention resist trapping specimen and cracking better than previous catalysts.

DETAILED DESCRIPTION OF THE EMBODIMENTS

Although the present invention will be described with respect to specific embodiments of combustion carbon analyzers, those skilled in the art will appreciate that changes can be made in form or detail without departing from the spirit or scope of the invention as defined in the appended claims.

Figure 1:
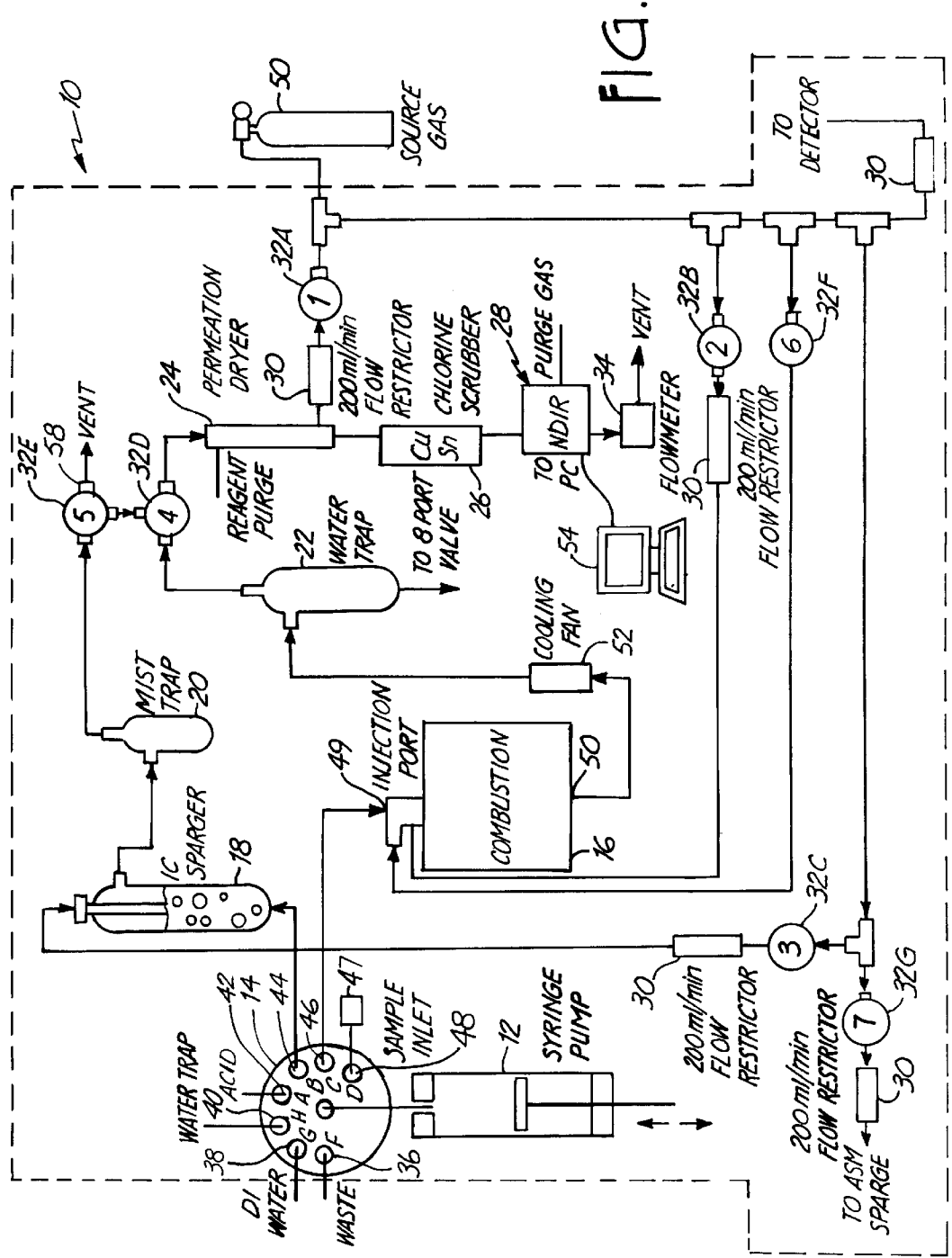
FIG. 1 is a system block diagram of a carbon analyzer in accordance with an embodiment of the invention.

FIG. 1 is a system block diagram of carbon analyzer 10 in accordance with an embodiment of the invention. Carbon analyzer 10 includes syringe pump 12, multiport valve 14, combustion chamber 16, inorganic carbon module 18, mist trap 20, water trap 22, dryer 24, scrubber 26, carbon dioxide detector 28, flow regulators 30, flow valves 32A–G, and flowmeter 34.

Analyzer 10 includes inorganic carbon module 18 which can remove inorganic carbon from a specimen in accordance with known methods. A specimen is any substance for which carbon analysis is desirable. A specimen can be provided to inorganic module 18 where an acid is combined with the specimen while carrier gas is bubbled through the specimen (sparged). This converts carbonate and bicarbonate in the specimen into carbon dioxide which may then be vented through vent 58, or measured by coupling inorganic carbon module 18 to carbon dioxide detector 28. Once inorganic carbon has been removed, module 18 can be selectively coupled to syringe pump 12 to draw the specimen into syringe pump 12 and pump the specimen into combustion chamber 16 for catalytic oxidation of the remaining carbon substances.

As will be described in greater detail later in the specification, combustion chamber 16 is operatively coupled to carbon dioxide detector 28 through cooling fan 52, water trap 22, flow valve 32D, dryer 24 and scrubber 26. Cooling fan 52 cools the carbon dioxide and water vapor produced from the catalytic oxidation within combustion chamber 16. Cooling fan 52 is coupled to water trap 22 to remove condensed water and provide such water to water trap port 40 of multiport valve 14. Carbon analysis of the removed water can provide an indication of the efficacy of catalytic oxidation in combustion chamber 16. Water trap 22 is coupled to dryer 24 to dehumidify the carbon dioxide in the specimen remaining after removal of condensed water. Dryer 24 is coupled to scrubber 26 to remove additional undesirable components, such as chlorine, which may remain after dehumidification. Scrubber 26 is coupled to carbon dioxide detector 28 which measures carbon dioxide and provides an indication of carbon quantity. In this manner analyzer 10 can provide data indicative of total carbon, inorganic carbon, and total organic carbon.

Sample inlet port 48 is shown as one of eight ports in multiport 14. Sample inlet port 48 is coupled to sample inlet 47, which disposed to receive a specimen. Multiport valve 14 can be any suitable valve where at least one port can be selectively coupled to at least one other port. Multiport valve 14 includes waste port 36, de-ionized (DI) water port 38, water trap port 40, acid port 42, inorganic carbon module port 44, combustion chamber port 46, and sample inlet port 48. Syringe pump 12 is coupled to multiport valve 14 such that syringe pump 12 can be selectively coupled to any of ports 36, 38, 40, 42, 44, 46 and 48. Depending on actuation direction, syringe pump 12 can either draw or pump fluid.

Figure 2:
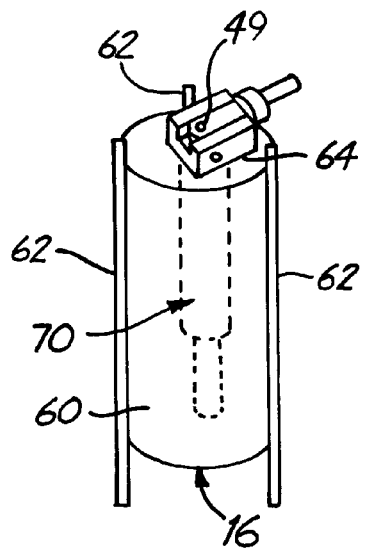
FIG. 2 is a perspective view of a combustion chamber in accordance with an embodiment of the invention.

Combustion chamber port 46 of multiport valve 14 is coupled to combustion chamber inlet 49 of combustion chamber 16. Combustion chamber 16 is any apparatus adapted for catalytically oxidizing specimens at temperatures ranging from about 670 degrees Celsius to about 1000 degrees Celsius. Combustion chamber 16 is also coupled to gas source 50 through flow valves 32-B and 32-F. Combustion chamber 16 can include an internal heat source or combustion chamber 16 can receive heat from an external source as appropriate. Combustion chamber 16 includes injection port 64 to selectively introduce specimen into combustion chamber 16. As shown in FIG. 2, combustion chamber 16 includes wall 60, supports 62, injection port 64, and platinum on titania catalyst 66 (shown in FIGS. 3 and 4). Wall 60 defines a chamber selectively coupled to combustion chamber inlet 49 of injection port 62, and a combustion chamber outlet 50. Supports 62 are coupled to wall 60 to support wall 60. Within combustion chamber 16, platinum on titania catalyst 66 is disposed in a combustion tube 70 such that catalyst 66 contacts the specimen to reduce the activation temperature of the specimen and thus increase catalytic oxidation effectiveness.

The catalyst includes a layer of platinum disposed on a titania substrate as will be described in greater detail later in the specification. Combustion chamber 16 catalytically oxidizes a specimen to provide carbon dioxide and water. The amount of carbon dioxide is related to the amount of carbon present in the specimen. The platinum on titania catalyst provides increased resistance to cracking and specimen trapping as well as provides more effective catalytic oxidation than known catalysts.

Carbon dioxide detector 28 is coupled to scrubber 26 to receive dehumidified carbon dioxide and provide an output indicative of carbon quantity. Detector 28 can be any suitable detector which provides an output indicative of carbon quantity. For example, detector 28 can be a non-dispersive infrared (NDIR) sensor. Detector 28 can also be coupled to flowmeter 34 and computer 54 such that carbon concentration can be conveniently calculated based upon carbon quantity and specimen flow.

Figure 3:
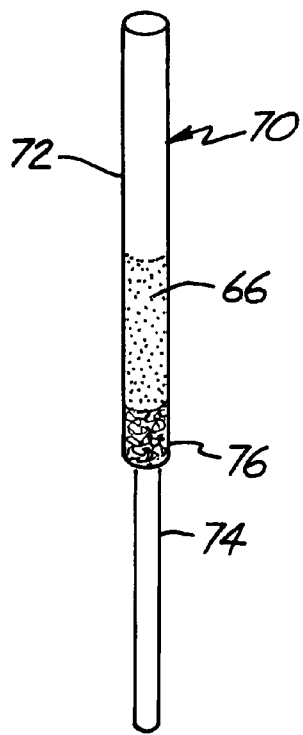
FIG. 3 is a perspective view of a combustion tube containing catalyst in accordance with an embodiment of the invention.

FIG. 3 is a perspective view of combustion tube 70 containing catalyst 66 in accordance with an embodiment of the invention. Combustion tube 70 is disposed within combustion chamber 16 (shown in phantom in FIG. 2) to provide a convenient container for catalyst 66 through which the specimen may flow. Combustion tube 70 is shown with a first portion 72 having a first diameter, and a second portion 74 having a second diameter which is smaller than the first diameter of portion 72. A quantity of quartz wool 76, or other suitable material, is provided in portion 72 to support catalyst 66 while allowing specimen to flow through combustion tube 70. Catalyst 66 is shown including a multiplicity of catalytic particles or members packed into combustion tube 70.

Figure 4:
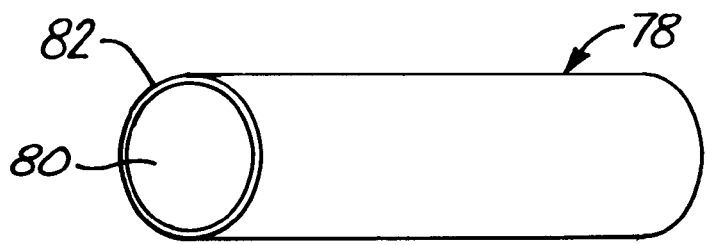
FIG. 4 is a perspective view of a catalytic member in accordance with an embodiment of the invention.

FIG. 4 is an enlarged perspective view of one of the many catalytic members shown in FIG. 3 in accordance with an embodiment of the invention. Member 78 can be cylindrically shaped, as shown in FIG. 4, or can be formed in other appropriate shapes such as spheres. Catalytic member 78 includes titania substrate 80 which is shown as a solid cylinder. A layer of platinum 82 is disposed on titania substrate 80. Platinum layer 82 can be disposed on titania substrate 80 in any suitable known manner such as electrodeposition. A platinum on titania catalyst can include any catalytic member or aggregate of catalytic members which have platinum operatively coupled to titania to reduce the activation temperature of specimens. In some embodiments, the weight of platinum layer 82 comprises about one percent of the total weight of catalytic member 78.

The platinum on titania catalyst resists cracking better than traditional platinum on alumina catalysts. The may be due in part to a smaller difference in coefficients of thermal expansion for platinum and titania compared to platinum and alumina. The coefficient of thermal expansion for platinum is $9 \times 10^{-6}/° C.$; alumina is about $5 \times 10^{31\ 6}/° C.$; and titania, in a form known as Rutile, is about $7 \times 10^{-6}/° C.$ By reducing cracking catalyst effectiveness and longevity are increased. Further, due to a less porous surface, a platinum on titania catalyst is less susceptible to trapping specimen in or on the catalyst surface. Trapping specimen is undesirable because subsequent analyses can be affected by the trapped specimen either by reduced catalytic effectiveness, or by erroneous carbon readings.

Figure 5:
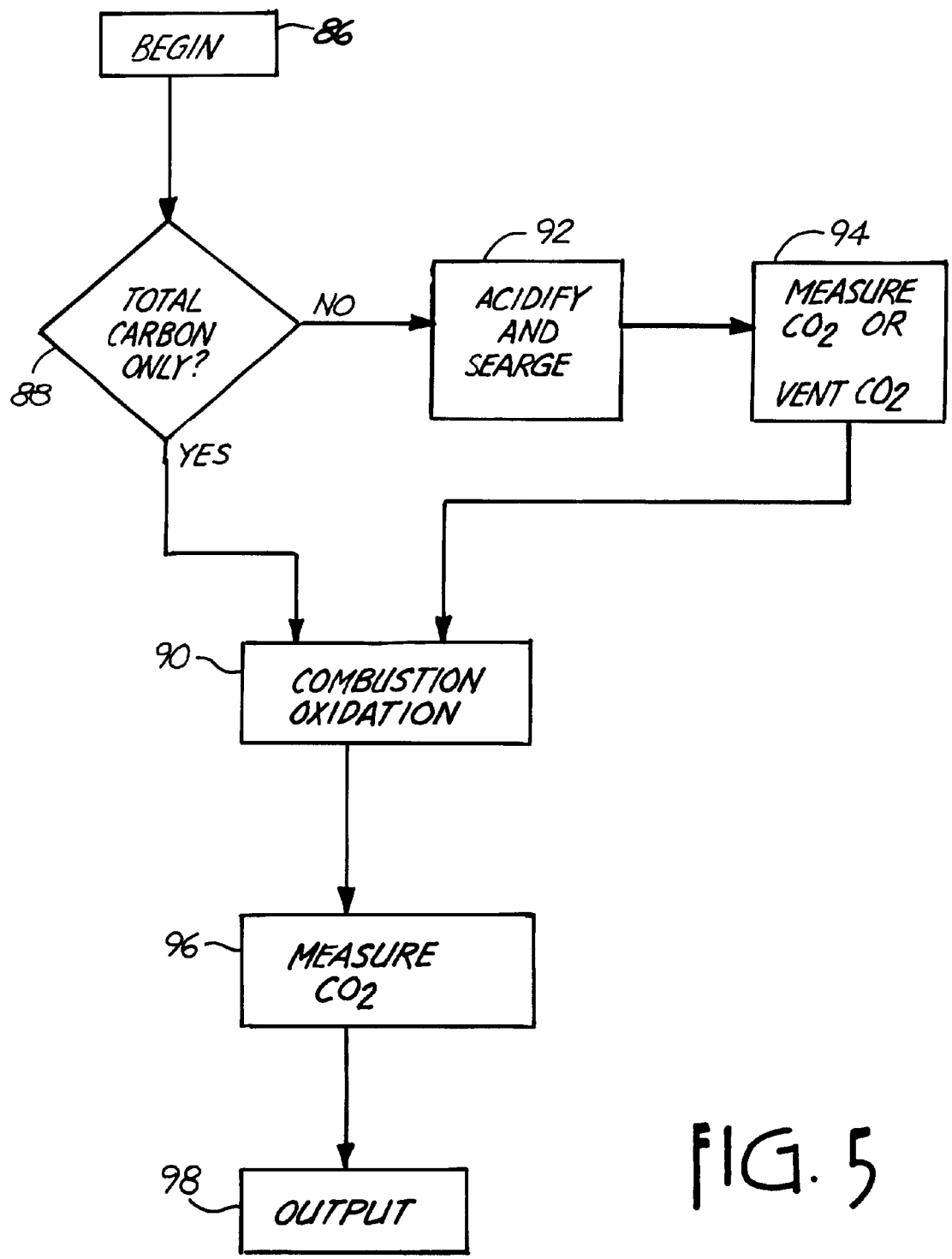
FIG. 5 is a flow diagram of steps performed in a method of analyzing a carbon-containing specimen in accordance with an embodiment of the invention.

FIG. 5 is a flow diagram of steps performed in a method of analyzing a carbon-containing specimen in accordance with an embodiment of the invention. The method begins at block 86 where the system is initialized. Control then passes to block 88 where analyzer 10 checks whether total carbon is the only quantity of interest, if so then control passes to combustion oxidation block 90, and if not control passes to sparge block 92. At block 92, an acid is added to the specimen while a carrier gas is bubbled through the specimen (sparging) to sweep away carbon dioxide converted from the inorganic carbon of the specimen. Analyzer 10 then passes from block 92 to block 94 where the carbon dioxide is either vented or measured as desired. Subsequently, analyzer 10 passes to block 90 where the specimen is catalytically oxidized in the presence of a platinum on titania catalyst at a temperature in the range of about 670 degrees Celsius to about 1000 degrees Celsius. During block 90, all remaining carbon in the specimen is theoretically converted to carbon dioxide.

After the catalytic oxidation of block 90, analyzer 10 passes to block 96 where the carbon dioxide is provided to a detector such as detector 28 for measurement. After the carbon dioxide has been measured, analyzer 10 passes to block 98 to provide an output related to the carbon dioxide quantity. optionally, specimen flow can be measured with a flowmeter such as flowmeter 34 so that carbon a concentration in the specimen can be provided as the output.

Figure 6:
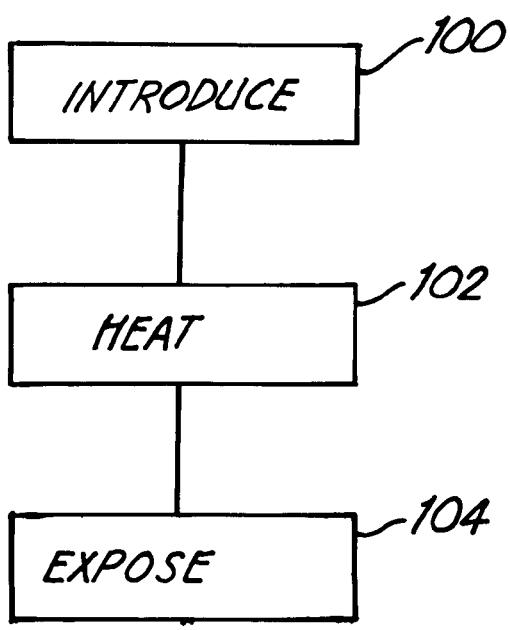
FIG. 6 is a flow diagram of steps performed in a method of catalytically oxidizing a carbon containing specimen in accordance with an embodiment of the invention.

FIG. 6 is a flow diagram of steps performed in a method of catalytically oxidizing a carbon containing specimen in accordance with an embodiment of the invention. The method begins at block 100 where a carbon-containing specimen is introduced into a combustion chamber for catalytic oxidation. At block 102, the specimen is heated to an elevated temperature in the range of about 670 degrees Celsius to about 1000 degrees Celsius. At block 104, the specimen is exposed to a platinum on titania catalyst to convert the specimen into water and carbon dioxide, thus catalytically oxidizing the specimen.

Figure 7:
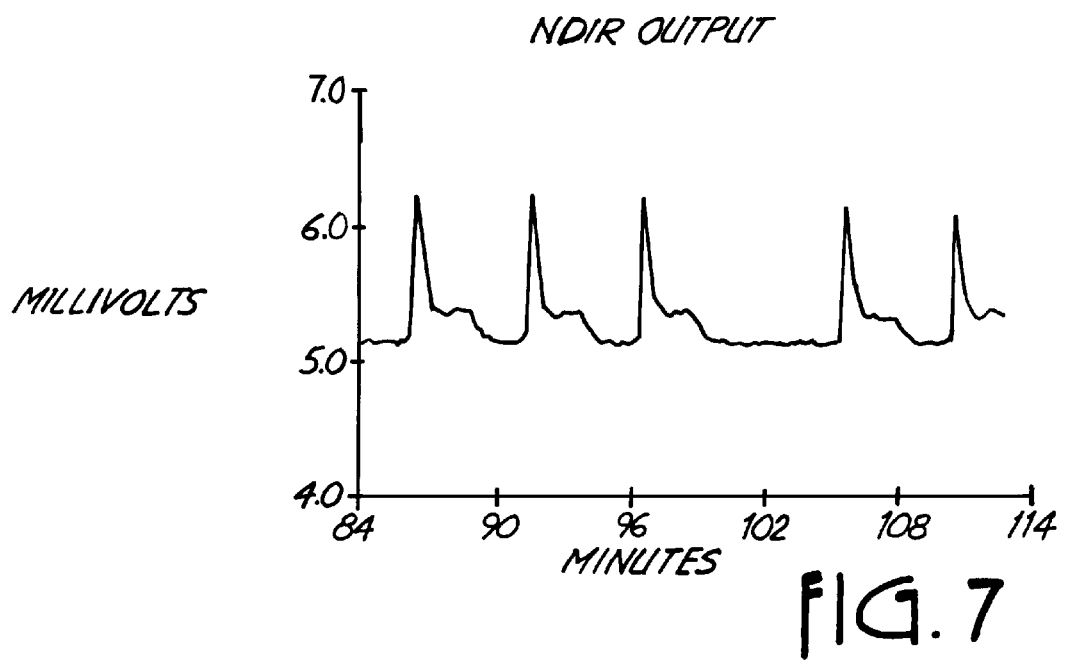
FIG. 7 is a chart showing carbon detector output as a function of time for a carbon analyzer in accordance with the prior art.
Figure 8:
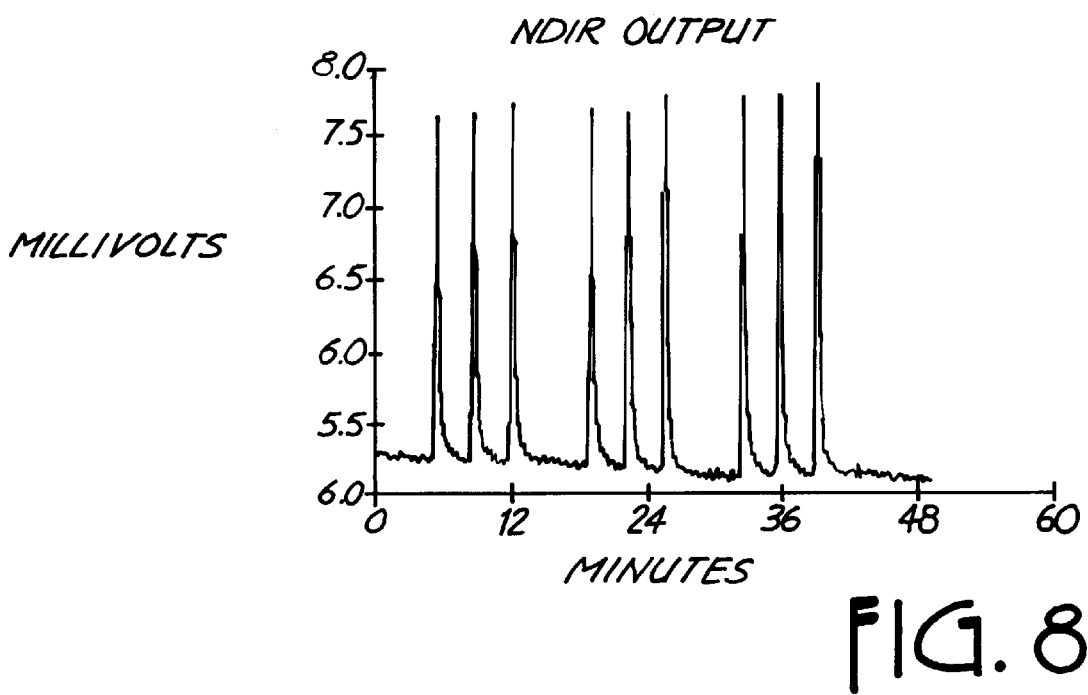
FIG. 8 is a chart showing carbon detector output as a function of time for a carbon analyzer in accordance with an embodiment of the invention.

FIGS. 7 and 8 are charts of carbon dioxide detector (NDIR) output expressed in millivolts as a function of time. FIG. 7 depicts detector output for traditional catalytic oxidation using a platinum on alumina catalyst for a 1.0 mL specimen having a carbon concentration of 0.1 parts per million (ppm). FIG. 7 shows a distinct chair-like shape to each peak. FIG. 8 depicts detector output for catalytic oxidation using a platinum on titania catalyst for a 1 mL specimen having a carbon concentration of 0.05 ppm. As can be seen, the peak shape shown in FIG. 8 is significantly different than that of FIG. 7. With a platinum on titania catalyst, the chair-like shape is removed, while the peaks are narrowed and raised. Note, even though the scales of FIGS. 7 and 8 are not identical, it can be appreciated that the 0.05 ppm carbon specimen oxidized with platinum on titania caused detector output signals larger than those of the 0.1 ppm carbon specimen oxidized with platinum on alumina. Thus, a catalyst in accordance with embodiments of the invention provides increased analyzer sensitivity while reducing cycle time and increasing throughput.

Figure 9:
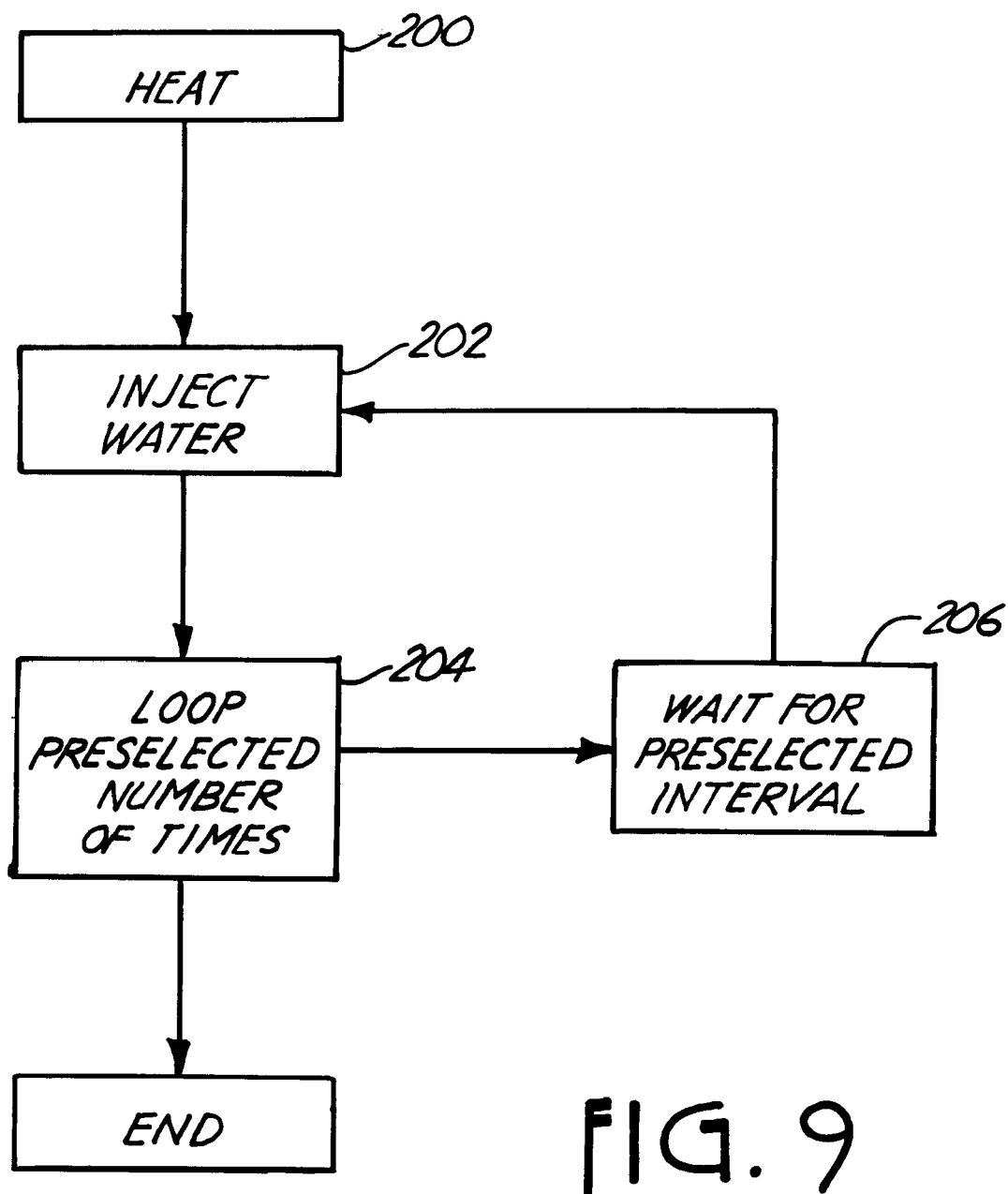
FIG. 9 is a flow diagram of steps performed in a method of conditioning a catalyst in accordance with an embodiment of the invention.

FIG. 9 is a flow diagram of steps performed in a method of conditioning a catalyst in accordance with an embodiment of the invention. When platinum-based catalyst is manufactured, it is possible for some carbon to be present in or on the catalyst itself. Such carbon could potentially affect specimen analysis if not removed. The method depicted in FIG. 9 conditions the catalyst by removing carbon from the catalyst itself prior to specimen analysis. The method begins at block 200 where the catalyst is heated to an elevated temperature above about 700 degrees Celsius, such as about 900 degrees Celsius. At block 202, a relatively small amount of water, such as about 0.1 mL is exposed to the heated catalyst. At block 204, the process is looped a pre-selected number cycles. During such iteration, control passes from block 204 to block 206, where the system waits a preselected interval before returning to block 202 for another water injection. The interval can be any appropriate duration, such as 1–3 minutes. When the method has looped the pre-selected number of times, such as 24 times, control passes to block 208 thus indicating that the conditioning method has finished. This method can be performed by a carbon analyzer such as analyzer 10 receiving water from a source such as de-ionized water port 38 of multiport valve 14. Alternatively, this method can be performed during catalyst manufacture.

What is claimed is:

1. A carbon analyzer comprising:

a sample inlet disposed to receive a specimen;

a combustion chamber having a chamber outlet and a chamber inlet operatively coupled to the sample inlet, the chamber disposed to catalytically oxidize the specimen at a temperature between about 670° C. and about 1000° C.;

a carbon dioxide detector operatively coupled to the chamber outlet and disposed to provide a detector output indicative of carbon quantity; and wherein the combustion chamber includes a catalyst comprising platinum and titania, the catalyst positioned to contact the specimen during catalytic oxidation.

2. The analyzer of claim 1, wherein the combustion chamber is adapted to operate at about 680 degrees Celsius.

3. The analyzer of claim 1, wherein the combustion chamber is adapted to operate at a temperature of about 1000 degrees Celsius.

4. The analyzer of claim 1, and further comprising:

a vent;

an inorganic carbon module operatively coupled to the sample inlet, the chamber inlet, the carbon dioxide detector and the vent, the inorganic carbon module disposed to convert at least one of carbonate and bicarbonate to carbon dioxide; and a valve selectively coupling the inorganic carbon module to one of the combustion chamber and the sample inlet.

5. The analyzer of claim 1, wherein the carbon dioxide detector comprises a non-dispersive infrared detector.

6. The analyzer of claim 1, wherein the catalyst includes a multiplicity of particles packed together, each particle including a platinum layer disposed on a titania substrate.

7. The analyzer of claim 6, wherein each particle is cylindrically shaped.

8. The analyzer of claim 1, wherein the catalyst is shaped cylindrically.

9. The analyzer of claim 1, wherein about one percent of the weight of the catalyst comprises platinum.

* * * * *